(12) United States Patent
Hollmén et al.

(10) Patent No.: US 10,884,000 B2
(45) Date of Patent: Jan. 5, 2021

(54) METHOD OF MONITORING THE EFFICACY OF THE ANTI-CLEVER-1 THERAPY IN CANCER

(71) Applicant: FARON PHARMACEUTICALS OY, Turku (FI)

(72) Inventors: Maija-Leena Hollmén, Piispanristi (FI); Miro Viitala, Turku (FI); Markku Jalkanen, Piispanristi (FI); Mikael Maksimow, Turku (FI)

(73) Assignee: Faron Pharmaceuticals Oy, Turku (FI)

( * ) Notice: Subject to any disclaimer, the term of this patent is extended or adjusted under 35 U.S.C. 154(b) by 0 days.

(21) Appl. No.: 16/093,349

(22) PCT Filed: Apr. 18, 2017

(86) PCT No.: PCT/FI2017/050286
§ 371 (c)(1),
(2) Date: Oct. 12, 2018

(87) PCT Pub. No.: WO2017/182706
PCT Pub. Date: Oct. 26, 2017

(65) Prior Publication Data
US 2019/0064180 A1  Feb. 28, 2019

(30) Foreign Application Priority Data

Apr. 18, 2016  (FI) ..................... 20165336

(51) Int. Cl.
| | | |
|---|---|---|
| G01N 33/68 | (2006.01) | |
| C07K 16/28 | (2006.01) | |
| G01N 33/50 | (2006.01) | |
| A61K 39/00 | (2006.01) | |

(52) U.S. Cl.
CPC ......... *G01N 33/6863* (2013.01); *C07K 16/28* (2013.01); *G01N 33/50* (2013.01); *A61K 2039/505* (2013.01); *C07K 2317/24* (2013.01); *G01N 2333/525* (2013.01); *G01N 2333/70539* (2013.01); *G01N 2333/7151* (2013.01); *G01N 2800/52* (2013.01)

(58) Field of Classification Search
None
See application file for complete search history.

(56) References Cited

FOREIGN PATENT DOCUMENTS

| WO | 03057130 A2 | 7/2003 |
|---|---|---|
| WO | 2010122217 A1 | 10/2010 |
| WO | 2014072441 A1 | 5/2014 |

OTHER PUBLICATIONS

Kzhyshkowska, J., "Multifunctional Receptor stabilin-1 in Homeostasis and Disease", The Scientific World Journal, Mini-Review, 2010, 10, pp. 2039-2053.
Noy, R. et al., "Tumor-Associated Macrophages: From Mechanism to Therapy", Immunity Review, 41, Jul. 17, 2014, pp. 49-61.
Finnish Search Report issued in Application No. 20165336 dated Jul. 29, 2016, 3 pages.
International Search Report and Written Opinion issued in Application No. PCT/FI2017/050286 dated Jul. 12, 2017, 11 pages.
Palani, S. et al., "Monocyte Stabilin-1 Suppresses the Activation of Th1 Lymphocytes", Journal of Immunology, Jan. 2016, vol. 196, No. 1, pp. 115-123.
Karikoski, M. et al., "Clever-1/Stabilin-1 Controls Cancer Growth and Metastasis", Clinical Cancer Research, Dec. 2014, vol. 20, No. 24, pp. 6452-6464.
Karikoski, M. et al., "Clever-1/Stabilin-1 regulates lymphocyte migration within lymphatics and leukocyte entrance to sites of inflammation", European Journal of Immunology, Oct. 2009, vol. 39, No. 12, pp. 3477-3487.
Kzhyshkowska, J. et al., "Perspectives for Monocyte/macrophage-Based Diagnostics of Chronic Inflammation", Transfusion Medicine and Hemotherapy, vol. 43, No. 2, Mar. 2016, pp. 66-77.
Buttari et al., "7-Oxo-cholesterol potentiates pro-inflammatory signaling in human M1 and M2 macrophages", Biochemical Pharmacology, Jul. 2013, vol. 86, No. 1, pp. 130-137.
Mulens-Arias, V. et al., "Polyethylenimine-coated SPIONs trigger macrophage activation through TLR-4 signaling and ROS production and modulate podosome dynamics", Biomaterials, Jun. 2015, vol. 52, pp. 494-506.
Domínguez-Soto, A. et al., "Intravenous Immunoglobulin Promotes Antitumor Responses by Modulating Macrophage Polarization", The Journal of Immunology, Nov. 2014, vol. 193, No. 10, pp. 5181-5189.
Li, Y. et al., "Low-dose cisplatin administration to septic mice improves bacterial clearance and programs peritoneal macrophage polarization to M1 phenotype", Pathogens and Disease, Nov. 2014, vol. 72, No. 2, pp. 111-123.
Palani, S. "Clever-1 as an Immune Suppresive Molecule", University of Turku, Mar. 18, 2016, XP055384491, pp. 1-72.
Palani, S. et al., "Stabilin-1/CLEVER-1, a type 2 macrophage marker, is an adhesion and scavenging molecule on human placental macrophages: Innate Immunity", European Journal of Immunology, vol. 41, No. 7, Jul. 1, 2011, pp. 2052-2063.
Communication pursuant to Article 94(3) EPC cited in EP 17 722 487.0 dated Jun. 24, 2020, 7 pages.
Palani et al., "Monocyte Stabilin-1 Suppresses the Activation of Th1 Lymphocytes", The Journal of Immunology, 2016, 196; Jan. 1, 2016, pp. 115-123.

*Primary Examiner* — Elly-Gerald Stoica

(74) *Attorney, Agent, or Firm* — Rothwell, Figg, Ernst & Manbeck, P.C.

(57) ABSTRACT

An agent capable of binding to CLEVER-1 in an individual can be used in activating macrophages to switch their phenotype from M2 macrophages into M1 macrophages. The invention relates to methods for utilizing the macrophages ability to switch their phenotype. In one aspect, the invention relates to a method for estimating of the efficacy of anti-CLEVER-1 therapy by monitoring a modulation of M2 macrophages into M1 macrophages, when an agent capable of binding to CLEVER-1 is administered in a patient, wherein an increased TNF-alpha secretion or HLA-DR expression is indicative of modulation of M2 macrophages into M1 macrophages.

4 Claims, 2 Drawing Sheets

Specification includes a Sequence Listing.

SEQUENCE LISTING

<160> NUMBER OF SEQ ID NOS: 7

<210> SEQ ID NO 1
<211> LENGTH: 15
<212> TYPE: PRT
<213> ORGANISM: Homo sapiens

<400> SEQUENCE: 1

Pro Phe Thr Val Leu Val Pro Ser Val Ser Ser Phe Ser Ser Arg
1               5                   10                  15

<210> SEQ ID NO 2
<211> LENGTH: 12
<212> TYPE: PRT
<213> ORGANISM: Homo sapiens

<400> SEQUENCE: 2

Gln Glu Ile Thr Val Thr Phe Asn Gln Phe Thr Lys
1               5                   10

<210> SEQ ID NO 3
<211> LENGTH: 10
<212> TYPE: PRT
<213> ORGANISM: Homo sapiens

<400> SEQUENCE: 3

Ala Thr Gln Thr Gly Arg Val Phe Leu Gln
1               5                   10

<210> SEQ ID NO 4
<211> LENGTH: 12
<212> TYPE: PRT
<213> ORGANISM: Homo sapiens

<400> SEQUENCE: 4

Asp Ser Leu Arg Asp Gly Arg Leu Ile Tyr Leu Phe
1               5                   10

<210> SEQ ID NO 5
<211> LENGTH: 13
<212> TYPE: PRT
<213> ORGANISM: Homo sapiens

<400> SEQUENCE: 5

Ser Lys Gly Arg Ile Leu Thr Met Ala Asn Gln Val Leu
1               5                   10

<210> SEQ ID NO 6
<211> LENGTH: 15
<212> TYPE: PRT
<213> ORGANISM: Homo sapiens

<400> SEQUENCE: 6

Leu Cys Val Tyr Gln Lys Pro Gly Gln Ala Phe Cys Thr Cys Arg
1               5                   10                  15

<210> SEQ ID NO 7
<211> LENGTH: 1051
<212> TYPE: PRT
<213> ORGANISM: Homo sapiens

<400> SEQUENCE: 7

Leu Cys Cys Ala Cys Leu Leu Glu Leu Ile Pro Tyr Ala Pro Thr Leu
1               5                   10                  15

-continued

```
Ser Trp Thr Ala Cys Pro Pro Ala Met Ala Gly Pro Arg Gly Leu Leu
            20                  25                  30
Pro Leu Cys Leu Leu Ala Phe Cys Leu Ala Gly Phe Ser Phe Val Arg
            35                  40                  45
Gly Gln Val Leu Phe Lys Gly Cys Asp Val Lys Thr Thr Phe Val Thr
 50                  55                  60
His Val Pro Cys Thr Ser Cys Ala Ala Ile Lys Lys Gln Thr Cys Pro
 65                  70                  75                  80
Ser Gly Trp Leu Arg Glu Leu Pro Asp Gln Ile Thr Gln Asp Cys Arg
                85                  90                  95
Tyr Glu Val Gln Leu Gly Gly Ser Met Val Ser Met Ser Gly Cys Arg
            100                 105                 110
Arg Lys Cys Arg Lys Gln Val Val Gln Lys Ala Cys Cys Pro Gly Tyr
            115                 120                 125
Trp Gly Ser Arg Cys His Glu Cys Pro Gly Gly Ala Glu Thr Pro Cys
            130                 135                 140
Asn Gly His Gly Thr Cys Leu Asp Gly Met Asp Arg Asn Gly Thr Cys
145                 150                 155                 160
Val Cys Gln Glu Asn Phe Arg Gly Ser Ala Cys Gln Glu Cys Gln Asp
                165                 170                 175
Pro Asn Arg Phe Gly Pro Asp Cys Gln Ser Val Cys Ser Cys Val His
            180                 185                 190
Gly Val Cys Asn His Gly Pro Arg Gly Asp Gly Ser Cys Leu Cys Phe
            195                 200                 205
Ala Gly Tyr Thr Gly Pro His Cys Asp Gln Glu Leu Pro Val Cys Gln
210                 215                 220
Glu Leu Arg Cys Pro Gln Asn Thr Gln Cys Ser Ala Glu Ala Pro Ser
225                 230                 235                 240
Cys Arg Cys Leu Pro Gly Tyr Thr Gln Gly Ser Glu Cys Arg Ala
                245                 250                 255
Pro Asn Pro Cys Trp Pro Ser Pro Cys Ser Leu Leu Ala Gln Cys Ser
                260                 265                 270
Val Ser Pro Lys Gly Gln Ala Gln Cys His Cys Pro Glu Asn Tyr His
            275                 280                 285
Gly Asp Gly Met Val Cys Leu Pro Lys Asp Pro Cys Thr Asp Asn Leu
290                 295                 300
Gly Gly Cys Pro Ser Asn Ser Thr Leu Cys Val Tyr Gln Lys Pro Gly
305                 310                 315                 320
Gln Ala Phe Cys Thr Cys Arg Pro Gly Leu Val Ser Ile Asn Ser Asn
                325                 330                 335
Ala Ser Ala Gly Cys Phe Ala Phe Cys Ser Pro Phe Ser Cys Asp Arg
            340                 345                 350
Ser Ala Thr Cys Gln Val Thr Ala Asp Gly Lys Thr Ser Cys Val Cys
            355                 360                 365
Arg Glu Ser Glu Val Gly Asp Gly Arg Ala Cys Tyr Gly His Leu Leu
            370                 375                 380
His Glu Val Gln Lys Ala Thr Gln Thr Gly Arg Val Phe Leu Gln Leu
385                 390                 395                 400
Arg Val Ala Val Ala Met Met Asp Gln Gly Cys Arg Glu Ile Leu Thr
                405                 410                 415
Thr Ala Gly Pro Phe Thr Val Leu Val Pro Ser Val Ser Ser Phe Ser
            420                 425                 430
Ser Arg Thr Met Asn Ala Ser Leu Ala Gln Gln Leu Cys Arg Gln His
```

```
                435                 440                 445
Ile Ile Ala Gly Gln His Ile Leu Glu Asp Thr Arg Thr Gln Gln Thr
            450                 455                 460

Arg Arg Trp Trp Thr Leu Ala Gly Gln Glu Ile Thr Val Thr Phe Asn
465                 470                 475                 480

Gln Phe Thr Lys Tyr Ser Tyr Lys Tyr Asp Gln Pro Gln Gln Thr
                485                 490                 495

Phe Asn Ile Tyr Lys Ala Asn Asn Ile Ala Ala Asn Gly Val Phe His
            500                 505                 510

Val Val Thr Gly Leu Arg Trp Gln Ala Pro Ser Gly Thr Pro Gly Asp
            515                 520                 525

Pro Lys Arg Thr Ile Gly Gln Ile Leu Ala Ser Thr Glu Ala Phe Ser
530                 535                 540

Arg Phe Glu Thr Ile Leu Glu Asn Cys Gly Leu Pro Ser Ile Leu Asp
545                 550                 555                 560

Gly Pro Gly Pro Phe Thr Val Phe Ala Pro Ser Asn Glu Ala Val Asp
                565                 570                 575

Ser Leu Arg Asp Gly Arg Leu Ile Tyr Leu Phe Thr Ala Gly Leu Ser
            580                 585                 590

Lys Leu Gln Glu Leu Val Arg Tyr His Ile Tyr Asn His Gly Gln Leu
            595                 600                 605

Thr Val Glu Lys Leu Ile Ser Lys Gly Arg Ile Leu Thr Met Ala Asn
            610                 615                 620

Gln Val Leu Ala Val Asn Ile Ser Glu Glu Gly Arg Ile Leu Leu Gly
625                 630                 635                 640

Pro Glu Gly Val Pro Leu Gln Arg Val Asp Val Met Ala Ala Asn Gly
                645                 650                 655

Val Ile His Met Leu Asp Gly Ile Leu Leu Pro Pro Thr Ile Leu Pro
            660                 665                 670

Ile Leu Pro Lys His Cys Ser Glu Gln His Lys Ile Val Ala Gly
            675                 680                 685

Ser Cys Val Asp Cys Gln Ala Leu Asn Thr Ser Thr Cys Pro Pro Asn
            690                 695                 700

Ser Val Lys Leu Asp Ile Phe Pro Lys Glu Cys Val Tyr Ile His Asp
705                 710                 715                 720

Pro Thr Gly Leu Asn Val Leu Lys Lys Gly Cys Ala Ser Tyr Cys Asn
                725                 730                 735

Gln Thr Ile Met Glu Gln Gly Cys Cys Lys Gly Phe Phe Gly Pro Asp
                740                 745                 750

Cys Thr Gln Cys Pro Gly Gly Phe Ser Asn Pro Cys Tyr Gly Lys Gly
            755                 760                 765

Asn Cys Ser Asp Gly Ile Gln Gly Asn Gly Ala Cys Leu Cys Phe Pro
            770                 775                 780

Asp Tyr Lys Gly Ile Ala Cys His Ile Cys Ser Asn Pro Asn Lys His
785                 790                 795                 800

Gly Glu Gln Cys Gln Glu Asp Cys Gly Cys Val His Gly Leu Cys Asp
                805                 810                 815

Asn Arg Pro Gly Ser Gly Val Cys Gln Gly Thr Cys Ala Pro
            820                 825                 830

Gly Phe Ser Gly Arg Phe Cys Asn Glu Ser Met Gly Asp Cys Gly Pro
            835                 840                 845

Thr Gly Leu Ala Gln His Cys His Leu His Ala Arg Cys Val Ser Gln
            850                 855                 860
```

```
Glu Gly Val Ala Arg Cys Arg Cys Leu Asp Gly Phe Glu Gly Asp Gly
865                 870                 875                 880

Phe Ser Cys Thr Pro Ser Asn Pro Cys Ser His Pro Asp Arg Gly Gly
                885                 890                 895

Cys Ser Glu Asn Ala Glu Cys Val Pro Gly Ser Leu Gly Thr His His
            900                 905                 910

Cys Thr Cys His Lys Gly Trp Ser Gly Asp Gly Arg Val Cys Val Ala
            915                 920                 925

Ile Asp Glu Cys Glu Leu Asp Met Arg Gly Gly Cys His Thr Asp Ala
    930                 935                 940

Leu Cys Ser Tyr Val Gly Pro Gly Gln Ser Arg Cys Thr Cys Lys Leu
945                 950                 955                 960

Gly Phe Ala Gly Asp Gly Tyr Gln Cys Ser Pro Ile Asp Pro Cys Arg
                965                 970                 975

Ala Gly Asn Gly Gly Cys His Gly Leu Ala Thr Cys Arg Ala Val Gly
            980                 985                 990

Gly Gly Gln Arg Val Cys Thr Cys Pro Pro Gly Phe Gly Gly Asp Gly
        995                 1000                1005

Phe Ser Cys Tyr Gly Asp Ile Phe Arg Glu Leu Glu Ala Asn Ala
    1010                1015                1020

His Phe Ser Ile Phe Tyr Gln Trp Leu Lys Ser Ala Gly Ile Thr
    1025                1030                1035

Leu Pro Ala Asp Arg Arg Val Thr Ala Leu Val Pro Ser
    1040                1045                1050
```

METHOD OF MONITORING THE EFFICACY OF THE ANTI-CLEVER-1 THERAPY IN CANCER

CROSS-REFERENCE TO RELATED APPLICATIONS

This application is a 35 U.S.C. § 371 National Stage of International Patent Application No. PCT/FI2017/050286, filed 18 Apr. 2017, designating the United States and claiming priority to Finnish application no. 20165336, filed on 18 Apr. 2016. The above identified applications are incorporated by reference.

FIELD OF INVENTION

The present invention relates to agents capable of binding to CLEVER-1 for use in immune activation and methods based thereon.

BACKGROUND OF THE INVENTION

The publications and other materials used herein to illuminate the background of the invention, and in particular, cases to provide additional details the practice, are incorporated by reference.

CLEVER-1 is a protein disclosed in WO 03/057130, Common Lymphatic Endothelial and Vascular Endothelial Receptor-1, also known as Stabilin-1 or Feel-1. CLEVER-1 has also been reviewed by Kzhyshkowska J. (2010), The Scientific World JOURNAL 10, 2039-2053. CLEVER-1 is expressed in lymphatic endothelial cells, certain vascular endothelial cells, but also in a subpopulation of macrophages. CLEVER-1 is a multifunctional molecule conferring scavenging ability on a subset of type 2 macrophages and human monocytes.

Macrophages play an important role in the growth or regression of tumours. The mechanisms of tumour-associated macrophages (TAMs) is disclosed e.g. in the publication by Noy R. and Pollard J. W., "Tumour-Associated Macrophages: From Mechanisms to Therapy", published in Immunity 41, Jul. 17, 2014, p. 49-61. M2 macrophages predominate in human cancers and stimulate tumour growth, but these tumour promoting macrophages can be modulated into tumour growth-inhibiting macrophages, called also as M1 macrophages or pro-inflammatory macrophages, aiming to slow or stop cancer growth. Consequently, the modulation of macrophage phenotype is a promising approach in immunotherapy of various cancers. However, it has been noticed that the attempts to treat cancers with the currently available therapeutics aiming at targeting TAMs were accompanied by undesired side effects, e.g. the macrophage therapeutic approaches may have systemic toxicities or paradoxically promote tumour growth, as they target all macrophages.

SUMMARY OF THE INVENTION

It has been found out that an agent capable of binding to human CLEVER-1 can be used to activate macrophages to switch their phenotype from M2 macrophages into M1 macrophages. Especially, an agent, such as an antibody and a fragment thereof, peptide(s) or macromolecule, capable of binding to CLEVER-1 on TAMs can be used to achieve a modulation of tumour promoting macrophages (M2) into pro-inflammatory macrophages (M1). The invention relates to methods for utilizing the macrophages ability to switch their phenotype.

Now, it is has been found out that a modulation of M2 macrophages into M1 macrophages can be monitored by measuring macrophage/monocyte TNF-alpha secretion and/or HLA-DR expression. Consequently, the present invention provides a method for monitoring and/or estimating the efficacy of anti-CLEVER-1 therapy in a patient.

The invention concerns a method for estimating of the efficacy of anti-CLEVER-1 therapy by monitoring the development of the modulation of M2 macrophages into M1 macrophages after an agent capable of binding to CLEVER-1 is administered in a patient, comprising the steps of (a) obtaining peripheral blood monocytes (PBLs) from a blood sample drawn from said patient,
(b) measuring the TNF-α secretion of said PBLs, and/or
(c) measuring HLA-DR expression on CD14 positive PBLs, and
(e) comparing values of the TNF-α secretion and/or the HLA-DR expression measured in steps (b) and (c) to the control values for an estimation of the efficacy of the anti-CLEVER-1 treatment, wherein the control values are the values measured before administering an agent capable of binding to CLEVER-1 in the patient or the values of one or more previous measurements carried out at different time points in the same patient and wherein an increased TNF-alpha secretion or HLA-DR expression is indicative of modulation of M2 macrophages into M1 macrophages.

In one aspect an agent capable of binding to CLEVER-1 in an individual is suitable for use in removing tumour or antigen immune suppression by modulating M2 macrophages into M1 macrophages. Preferably, the present invention concerns an agent, such as an antibody or a fragment thereof, peptide(s) or macromolecule(s), capable of binding to an epitope on CLEVER-1 molecule, wherein the epitope is discontinuous and comprises the sequences:

```
                                           (SEQ ID NO: 1)
    PFTVLVPSVSSFSSR,
    and (SEQ ID NO: 2)
    QEITVTFNQFTK of human CLEVER-1.
```

The modulation of macrophages phenotype increases T-cell activation and eventually leads e.g. to removal of cancer originated immune suppression. Consequently, the present finding provides a method for affecting the immune system in an individual and is especially useful in treating cancer or preventing metastasis, but not limited to this approach. Thus, an agent, such an antibody or a fragment thereof, peptide(s) or macromolecule, capable of binding to CLEVER-1 on TAMs, preferably to specific sequences on CLEVER-1 molecule, is suitable for use in the treatment of cancer or in preventing metastasis in an individual, wherein immune suppression around malignant growth is removed by modulating M2 macrophages into M1 macrophages.

An agent, such an antibody or a fragment thereof, peptide(s) or macromolecule(s), capable of binding to CLEVER-1, preferably to specific sequences on CLEVER-1 molecule, is also suitable for use in treatment of chronic infections in an individual, wherein immune suppression against the infective antigens is removed by modulating M2 macrophages into M1 macrophages.

Therefore, the method according to the invention for estimating of the efficacy of anti-CLEVER-1 therapy may especially be applied when the agent capable of binding to CLEVER-1 is administered in a patient for use in treating cancer or preventing metastasis, or treating chronic infections.

Further, an agent capable of binding to CLEVER-1, preferably to specific sequences on CLEVER-1 molecule, is also suitable for use as an adjuvant of a vaccine, wherein immune suppression against vaccine antigens is removed by modulating M2 macrophages into M1 macrophages.

In another aspect, the invention concerns a method for modulating M2 macrophages into M1 macrophages comprising administering to a subject in need thereof an agent capable of binding to CLEVER-1, preferably binding to specific sequences on CLEVER-1 molecule disclosed in the present application. Further, the invention concerns use of said method for modulating M2 macrophages into M1 macrophages in treatment of cancer or in preventing metastasis in an individual, or in treatment of chronic infections in an individual.

DEFINITIONS AND DETAILED DESCRIPTION OF THE INVENTION

Figure 1:
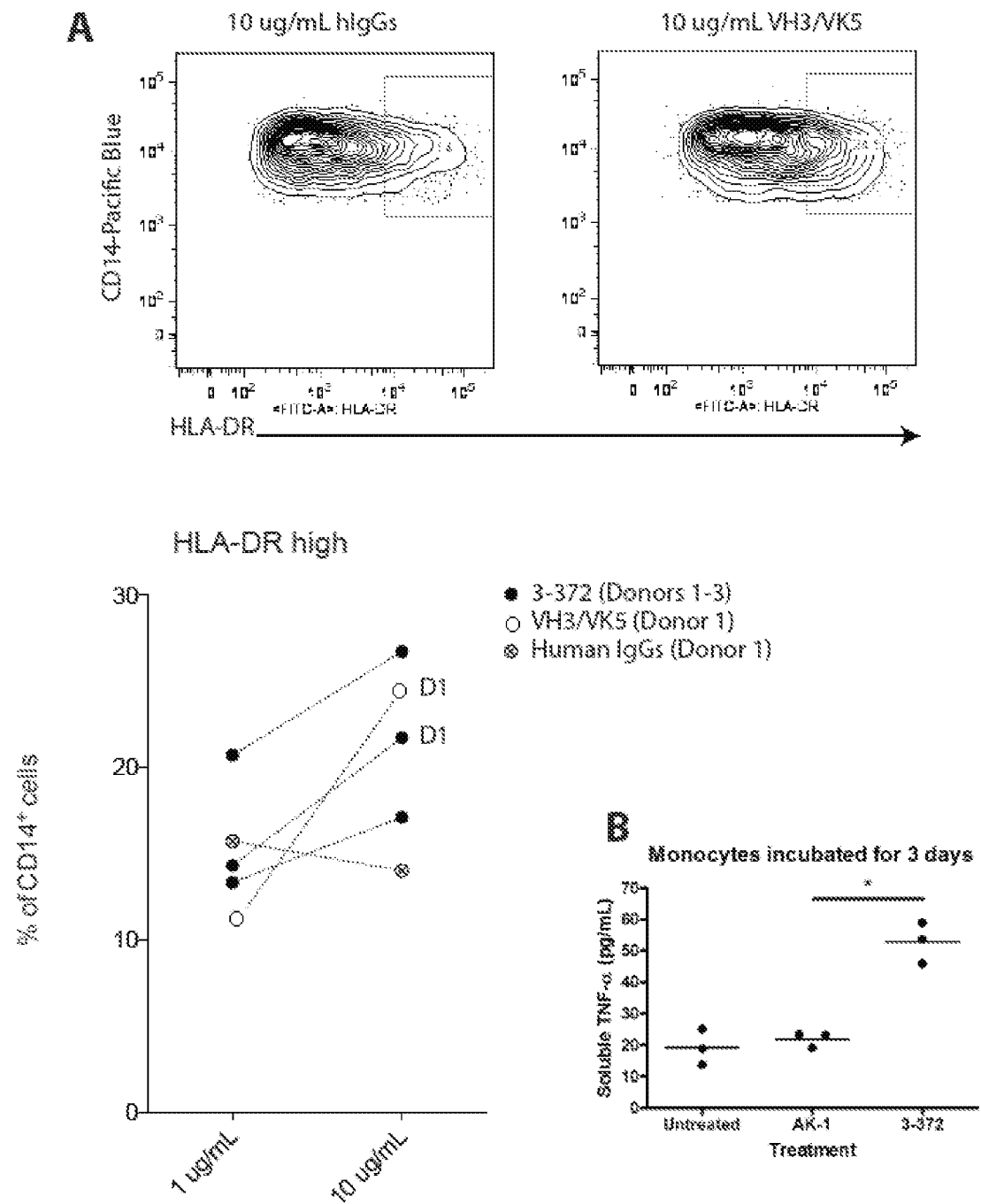
FIG. 1A shows results of the determination of HLA-DR expression from CD14 positive cells. The cells were treated with human IgGs or the CLEVER-1 targeting humanized antibodies VH3/VK5. The method used for determining HLA-DR expression from CD14 positive cells is presented detailed in the experimental part.
FIG. 1B shows results of soluble TNF-alpha measured from the culture medium using a TNF-alpha ELISA kit (Invitrogen).

The term "CLEVER-1" is used to denote the protein disclosed in WO 03/057130, Common Lymphatic Endothelial and Vascular Endothelial Receptor-1.

The term "an agent capable of binding to human CLEVER-1" refers to agents including antibodies and fragments thereof or peptides or the like, which are capable of binding to human CLEVER-1. The agent may also be any other macromolecule having an adequate affinity to bind to a specific epitope of human CLEVER-1 defined in the present application.

The term "an antibody or a fragment thereof" is used in the broadest sense to cover an antibody or a fragment thereof which are capable to bind CLEVER-1 molecule in an individual. Especially, it shall be understood to include chimeric, humanized or primatized antibodies, as well as antibody fragments and single chain antibodies (e.g. Fab, Fv), so long they exhibit the desired biological activities.

Particularly preferred CLEVER-1 antagonist monoclonal antibodies 3-266 (DSM ACC2519) and 3-372 (DSM ACC2520), both deposited under the terms of the Budapest Treaty on the International Recognition of the Deposit of Micro-organisms for the Purposes of Patent Procedure on Aug. 21, 2001, with DSMZ-Deutsche Sammlung von Mikroorganismen and Zellkulturen GmbH, Mascheroder Weg 1b, D-38124 Braunschweig, are disclosed in WO 03/057130.

The term "patient" or "individual" refers to a human.

The term "treatment" or "treating" shall be understood to include complete curing of a disease as well as amelioration or alleviation of said disease. The term "prevention" shall be understood to include complete prevention, prophylaxis, as well as lowering the individual's risk of falling ill with said disease or disorder.

Macrophages may be divided into two distinct phenotypes: M1 and M2 macrophages. M1 macrophages are classical pro-inflammatory macrophages, which produce large quantities of pro-inflammatory cytokines and co-stimulatory molecules, and are very efficient in activation of T-cell responses. M2 macrophages, in contrast, are immune suppressing cells, which synthesize anti-inflammatory cytokines and induce regulatory T cells and hence profoundly dampen antigen-driven T cell activation. Tumour-associated macrophages (TAMs) are considered harmful as they mature into M2 macrophages (tumour promoting macrophages) within the tumour environment and suppress anti-tumour immune response and mediate angiogenic switch, a crucial step in cancer growth. The M2 macrophages can be modulated into M1 macrophages (pro-inflammatory macrophages) and such phenotype conversion from M2 to M1 may directly or indirectly cause tumour rejection.

In the present context the expression "M1 macrophages" or "pro-inflammatory macrophages" refers to the macrophages characterized by an increased measured level of macrophage/monocyte TNF-alpha (TNF-$\alpha$) secretion or HLA-DR expression. The modulation of M2 macrophages into M1 macrophages will increase monocyte TNF-alpha secretion and also HLA-DR expression compared to the control values measured before administering an agent capable of binding to CLEVER-1 in the patient, or the values of one or more previous measurements carried out at different time points in the same patient. It is important to compare measured values of monocyte TNF-alpha secretion and HLA-DR expression to the values of the same patient, since the level of these markers may vary from an individual to another and e.g. cytokines such as interferon-gamma and LPS activation may increase TNF-alpha expression by the M2 macrophages.

It has surprisingly been found that M2 macrophages can be activated to modulate M1 macrophages by contacting the said macrophages by an agent capable of binding to human CLEVER-1. Especially it has been found out that the M2 macrophages associated with malignant tumours can be modulated or re-polarized into M1 macrophages by contacting the said macrophages by an agent capable of binding to CLEVER-1 on TAMs. Both phenotypes can be present at same time and both of the phenotypes can be found in tumours.

An agent, such as an antigen or a fragment thereof, peptide(s) or macromolecule, is bound to human CLEVER-1 for achieving said modulation or re-polarization of macrophage phenotypes. It has been identified that agents such as antibodies specific for CLEVER-1 protein recognize a specific CLEVER-1 epitope. Consequently, an agent is preferably bound to specific sequences, i.e. epitopes, on the CLEVER-1 molecule for achieving said modulation of macrophage phenotypes, wherein the epitope is discontinuous and comprises the amino acid sequences:

```
                                          (SEQ ID NO: 1)
PFTVLVPSVSSFSSR,
and (SEQ ID NO: 2)
QEITVTFNQFTK of human CLEVER-1.
```

In some embodiments of the invention the discontinuous epitope further comprises one or more of amino acid sequences selected from the group consisting of:

```
                                          (SEQ ID NO: 3)
ATQTGRVFLQ, (SEQ ID NO: 4)
DSLRDGRLIYLF, (SEQ ID NO: 5)
SKGRILTMANQVL,
and (SEQ ID NO: 6)
LCVYQKPGQAFCTCR of human CLEVER-1.
```

A part of the target protein human CLEVER-1, i.e. human Stabilin-1, has defined in SEQ ID NO: 7. The epitopes SEQ ID NO: 1, SEQ ID NO: 2, SEQ ID NO: 3, SEQ ID NO: 4, SEQ ID NO: 5 and SEQ ID NO: 6 on the CLEVER-1 molecule corresponds amino acids 420-434, 473-484, 390-399, 576-587, 615-627 and 313-327 of target protein human CLEVER-1 defined in SEQ ID NO: 7. A discontinuous epitope mapping of human CLEVER-1 is disclosed more detailed in Finnish patent application No. 20165335.

A specific binding to two or more said epitope sequences on CLEVER-1 on TAMs will provide a novel method for treating cancers or preventing metastasis without harmful side-effects since the treatment can be targeted to specific epitopes for achieving desired modulation of macrophage phenotype. Consequently, the findings described here are especially useful in the treatment or prevention of all kinds of malignant tumours associated with an increased amount of tumour promoting macrophages or other pathologies such as chronic inflammation where an individual presents a dominance of immune suppression. Consequently, a method for treating cancer or preventing metastasis comprising administering to an individual an antibody or a fragment thereof binding to CLEVER-1, preferably to specific epitopes on CLEVER-1 molecule defined above. The method comprises treating or preventing cancer by reducing tumour size and/or; by reducing tumour growth in an individual; and/or by inhibiting cancer cell transmigration and metastasis formation. Thus, any benign or malignant tumour or metastasis of malignant tumour, such as skin cancer and colon cancer can be treated. Also leukemias, lymphomas and multiple myelomas can be treated. Particularly, melanomas and lymphomas are expected to respond very well to the treatment based on animal models.

The method for modulating macrophages phenotype is believed to be useful in the treatment or prevention of all kinds of sarcomas, such as fibrosarcoma, liposarcoma, chondrosarcoma, osteosarcoma, angiosarcoma, lymphangiosarcoma, leiomyosarcoma, and rhabdomyosarcoma, mesothelioma, meningioma, leukemias, lymphomas, as well as all kinds of carcinomas, such as squamous cell carcinomas, basal cell carcinoma, adenocarcinomas, papillary carcinomas, cystadenocarcinomas, bronchogenic carcinomas, melanomas, renal cell carcinomas, hepatocellular carcinoma, transitional cell carcinomas, choriocarcinomas, seminomas, and embryonal carcinomas.

Macrophages have also an important role during inflammation and infection resolution besides affecting in the growth or regression of tumours. In infections, a switch from M1 to M2 macrophage can occur, leading to the generation of suppressive environment that abrogates effector immunity. Consequently, the findings described here to modulate macrophages phenotype are also useful in the treatment of chronic infections to remove immune suppression against the infective antigens. A method for treating chronic infections comprising administering to an individual an agent capable of binding to CLEVER-1, preferably to two or more specific epitope sequences on CLEVER-1 molecule defined above, wherein said agent may activate macrophages to switch their phenotype from M2 into M1.

Further, an agent capable of binding to CLEVER-1 molecule on macrophages and monocytes in an individual can be used as an adjuvant in vaccines. The said agent achieves re-polarization of macrophages and thus removes or at least decreases immune suppression against the vaccine antigens. Any antigen-induced vaccination may benefit if the host or vaccination site can temporally be removed from immune suppressive elements.

A pharmaceutical composition comprising an agent capable of binding to CLEVER-1 and an appropriate excipient is suitable for use in treating or preventing cancer, or in treating chronic infections. The pharmaceutical compositions to be used in the present invention can be administered by any means that achieve their intended purpose. For example, administration can be intravenous, intraarticular, intra-tumoural or subcutaneous. In addition to the pharmacologically active compounds, the pharmaceutical preparations of the compounds preferably contain suitable pharmaceutically acceptable carriers comprising excipients and auxiliaries that facilitate processing of the active compounds into preparations that can be used pharmaceutically.

The modulation of M2 into M1 macrophages may be verified by measuring monocyte TNF-alpha secretion from human blood samples. Consequently, the increased secretion of TNF-alpha may be used as a marker for monitoring treatment response in an individual. The TNF-alpha secretion may be determined from the peripheral blood monocytes enriched from the blood drawn from a patient. A level of the TNF-alpha measured may be used as a marker for the patient response to the treatment comprising administering an agent capable of binding to human CLEVER-1, when the level is compared to control level measured from the same patient before administering said agent capable of binding to CLEVER-1 in the patient, or the values of one or more previous measurements carried out at different time points in the same patient.

According to an embodiment of the invention, a method for estimating of the efficacy of anti-CLEVER-1 therapy by monitoring a development of a modulation of M2 macrophages into M1 macrophages, when an agent capable of binding to CLEVER-1, preferably to said two or more specific epitope sequences on CLEVER-1, is administered in a patient, comprising the steps of
 (a) obtaining peripheral blood monocytes (PBLs) from a blood sample drawn from said patient,
 (b) measuring the TNF-α secretion of said PBLs, and/or
 (c) measuring HLA-DR expression on CD14 positive PBLs, and
 (e) comparing values of the TNF-α secretion and/or the HLA-DR expression measured in steps (b) and (c) to control values for an estimation of the efficacy of the anti-CLEVER-1 treatment, wherein the control values are the values measured before administering an agent capable of binding to CLEVER-1 in the patient or the values of one or more previous measurements carried out at different time points in the same patient and wherein an increased TNF-alpha secretion or HLA-DR expression is indicative of modulation of M2 macrophages into M1 macrophages.

Determining of TNF-alpha secretion from peripheral blood monocytes obtained from a blood sample drawn from the patient can be carried commonly known methods, for example by using a commercial TNF-alpha ELISA kit. The HLA-DR expression on CD14 positive monocytes can also be monitored by using a known method by flow cytometry.

The development of modulation of M2 macrophages into M1 macrophages may be monitored by comparing a measured level of monocyte TNF-alpha secretion to the control values measured before administering an agent capable of binding to CLEVER-1 in the patient, or the values of one or more previous measurements carried out at different time points in the same patient. For example, a decreased level of monocyte TNF-alpha secretion compared to the results from previous measurements or to a control may be used to indicate higher expression of M2 macrophages, while an increased level of TNF-alpha, compared to the results from previous measurements or to a control may be used to indicate that more expression of M1 macrophages with lower expression of M2 macrophages, wherein it can also be used to indicate the efficacy of the anti-CLEVER-1 treatment. The increased level of TNF-alpha indicates more expression of M1 macrophages with lower expression of M2 macrophages, i.e. it attributes responsiveness to said therapy. An agent capable of binding to CLEVER-1 will activate at least a part of the M2 macrophages to re-polarize into M1 macrophages and after the administration of said agent both macrophage phenotypes may be present, but the increased expression of the M1 macrophages may be observed compared to the situation before the administration of said agent.

According to an embodiment of the invention, at least a two fold increase of the measured TNF-alpha secretion compared to the control value is indicative of modulation of M2 macrophages into M1 macrophages and so to indicate the patient responsiveness to the therapy.

The invention is illustrated by the following non-limiting examples. It should be understood that the embodiments given in the description above and the examples are for illustrative purposes only, and that various changes and modifications are possible within the scope of the invention.

EXAMPLES

Example 1: Antibody Binding In Vitro

Human peripheral blood monocytes from healthy donors were collected and they were enriched from about 9 ml of peripheral blood by Ficoll-gradient centrifugation. After that they are plated in low attachment 96-well plates in a density of $1.2 \times 10^6$ cell/well in IMDM medium supplemented with 1% human AB serum. The cells were treated with 1 µg/ml or 10 µg/ml of anti-CLEVER-1 antibody 3-372 (DSM ACC2520 deposited at DSMZ-Deutsche Sammlung von Mikroorganismen und Zellkulturen GmbH on Aug. 21, 2001) or VH3/VK5 (a humanized anti-CLEVER-1 antibody recognizing said specific CLEVER-1 epitopes, details of the antibody is presented more detailed in below, DSM ACC3361 deposited at DSMZ-Deutsche Sammlung von Mikroorganismen und Zellkulturen GmbH, Inhoffenstrasse 7B, D-38124 Braunschweig, Germany on May 27, 2020) for 48 hours. HLA-DR expression was determined from CD14 positive cells after 48 hours by using LSR Fortessa flow cytometry. Dead cells were eliminated from the analysis based on the positive signal for 7-AAD cell viability dye.

Human IgGs was used as reference.

FIG. 1A shows results of the determination HLA-DR expression from CD14 positive cells. HLA-DR expression on CD14 positive cells increased with treatment of humanized anti-CLEVER-1 antibody VH3/VK5 compared to reference of human IgGs.

No difference in cell viability between treatments was observed. Thus, it can be concluded that the CLEVER-1 targeting antibodies do not affect monocyte survival.

A Humanized Anti-CLEVER-1 Antibody VH3/VK5

A humanized anti-CLEVER-1 antibody VH3/VK5 is generated from the 3-372 mouse monoclonal antibody (DSM ACC2520 deposited at DSMZ-Deutsche Sammlung von Mikroorganismen und Zellkulturen GmbH on Aug. 21, 2001) using Composite Human Antibody™ technology, which is disclosed more detailed in Finnish patent application FI 20165335. The humanized anti-CLEVER-1 antibody VH3/VK5 recognizing epitope sequences of human CLEVER-1 defined in the present application.

Example 2: Measurement of TNF-α

Human peripheral blood monocytes from healthy donors were collected and enriched as described in Example 1. Monocytes from 3 ml of erythrocyte lysis buffer treated blood were let to adhere overnight on 6-well plates, washed once with PBS and cultured for 3 days with 10 µg/ml of anti-CLEVER-1 antibody 3-372 or AK-1.

Soluble TNF-alpha was measured from culture medium using a commercial TNF-alpha ELISA kit (Invitrogen). The results of the measurement are showed in FIG. 1B. The increased TNF-alpha secretion has noticed by samples treated with anti-CLEVER-1 antibody compared to untreated samples or the control treated samples with AK-1.

Example 3: Mouse Syngeneic Cancer Models

Established E0771 mouse mammary carcinomas were treated with 5 mg/kg of anti-CLEVER-1 (mStab1) or isotype control every 3-4 days until the tumours reached a size of 1 mm$^3$. The effect of anti-CLEVER-1 treatment on the recruitment and phenotype of TAMs, different monocyte subsets and tumour-infiltrating leukocytes was assessed using flow cytometry.

Figure 2:
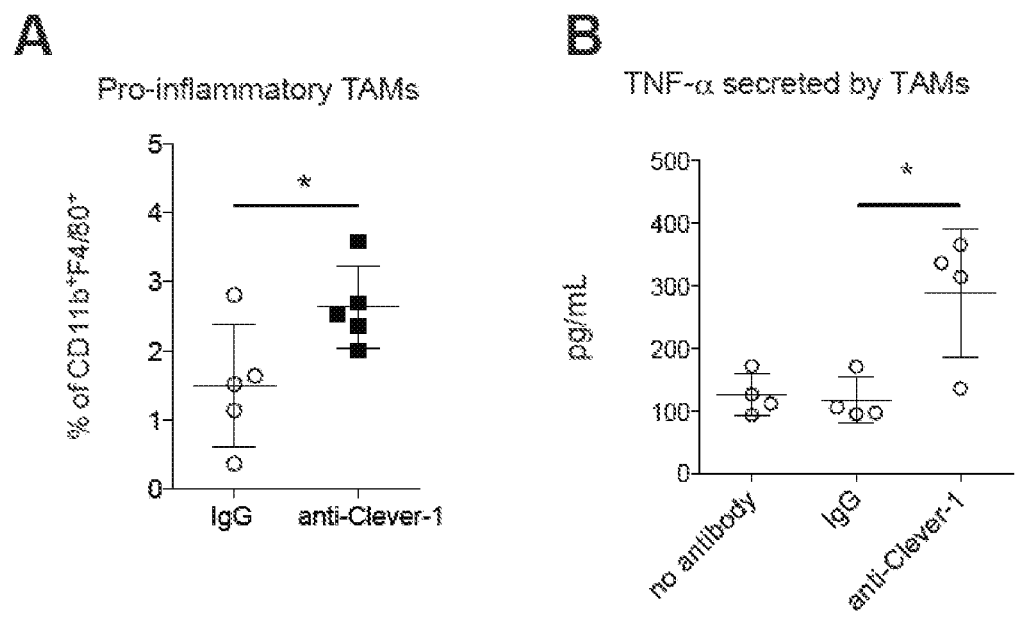
FIG. 2A shows TAM re-polarization in syngeneic E0771 mammary carcinomas after administration of an antibody binding to CLEVER-1. TAM re-polarization is measured by increased macrophage populations expressing MHCII (in human HLA-DR) by flow cytometry. Each dot represents the percentage of $MHCII^{high}$ $CD11b^+F4/80^+$ TAMs in one mouse.
FIG. 2B shows increased secretion of TNF-alpha on TAMs from E0771 syngeneic mammary carcinoma after administration of an antibody binding to CLEVER-1. Each dot represents TAMs isolated from one mouse.

FIG. 2A shows TAM re-polarization in syngeneic E0771 mammary carcinomas after administration of an antibody binding to CLEVER-1. Tumours treated with anti-CLEVER-1 showed a similar level of TAMs (CD11b$^+$F4/80$^+$) compared to the control treated tumours. However, the TAM population in anti-CLEVER-1 tumours consisted of more pro-inflammatory macrophages (Ly6C$^{lo}$MHCII$^{hi}$) with lower expression of the type II marker, CD206.

The anti-CLEVER-1 treated TAMs secreted significantly more TNF-alpha compared to IgG treated TAMs, as shown in FIG. 2B. Consistent with this, also a decrease in FoxP3$^+$ tumour-infiltrating leukocytes was observed.

The results indicate that CLEVER-1 is a potential target for macrophage-directed immunotherapy and that the efficiency of anti-CLEVER-1 treatment could be monitored by monocyte TNF-α secretion.

The invention claimed is:

1. A method for monitoring the modulation of M2 macrophages into M1 macrophages as an indication of the efficacy of an anti-CLEVER-1 therapy, comprising the steps of
   (a) administering an agent capable of binding to CLEVER-1 to a patient in need of such treatment,
   (b) obtaining peripheral blood monocytes (PBLs) from a blood sample drawn from said patient,
   (c) measuring the TNF-alpha secretion of said PBLs, and
   (d) measuring HLA-DR expression on CD14 positive PBLs,
   (e) comparing values of the TNF-alpha secretion and the HLA-DR expression measured in steps (c) and (d) to control values for an estimation of the efficacy of the anti-CLEVER-1 treatment, wherein the control values are the values measured before administering an agent capable of binding to CLEVER-1 in the patient or the values of one or more previous measurements carried out at different time points in the same patient and wherein an increased TNF-alpha secretion and HLA-DR expression is indicative of modulation of M2 macrophages into M1 macrophages, and
   (f) continuing the anti-CLEVER-1 treatment if an increased TNF-alpha secretion or HLA-DR expression is determined, wherein the agent capable of binding to CLEVER-1 binds to an epitope of human CLEVER-1 wherein the epitope comprises the sequences:
   PFTVLVPSVSSFSSR (SEQ ID NO: 1), and
   QEITVTFNQFTK (SEQ ID NO: 2), and
   wherein the agent capable of binding to CLEVER-1 is anti-CLEVER-1 antibody 3-372 or VH3/VK5.

2. The method according to claim 1, wherein the epitope further comprises one or more of sequences selected from the group consisting of:
   ATQTGRVFLQ (SEQ ID NO: 3),
   DSLRDGRLIYLF (SEQ ID NO: 4),
   SKGRILTMANQVL (SEQ ID NO: 5), and
   LCVYQKPGQAFCTCR (SEQ ID NO: 6).

3. The method according to claim 1, wherein at least a two fold increase of the measured TNF-alpha secretion compared to the control value is indicative of a modulation of M2 macrophages into M1 macrophages.

4. The method according to claim 1, wherein said patient is suffering from cancer originated tumor or antigen immune suppression.

* * * * *